United States Patent

Rick et al.

(10) Patent No.: US 6,714,621 B2
(45) Date of Patent: Mar. 30, 2004

(54) METHOD AND APPARATUS FOR RADIOLOGICAL EXAMINATION BY INJECTION OF A CONTRAST MEDIUM

(75) Inventors: Andreas Rick, Plaisir (FR); Serge Muller, Guyancourt (FR)

(73) Assignee: GE Medical Systems Global Technology Company LLC, Waukesha, WI (US)

( * ) Notice: Subject to any disclaimer, the term of this patent is extended or adjusted under 35 U.S.C. 154(b) by 68 days.

(21) Appl. No.: 09/900,576

(22) Filed: Jul. 6, 2001

(65) Prior Publication Data

US 2002/0003861 A1 Jan. 10, 2002

(30) Foreign Application Priority Data

Jul. 7, 2000 (FR) .......................... 00 08870

(51) Int. Cl.[7] .............................. H05G 1/64
(52) U.S. Cl. ................ 378/98.12; 378/18; 378/37; 378/62
(58) Field of Search .............. 378/18, 37, 62, 378/64, 98.2, 98.7, 98.11, 98.12, 98.8

(56) References Cited

U.S. PATENT DOCUMENTS

| | | | |
|---|---|---|---|
| 3,854,049 A | * 12/1974 | Mistretta et al. | 378/62 |
| 4,335,427 A | * 6/1982 | Hunt et al. | 600/407 |
| 4,672,651 A | * 6/1987 | Horiba et al. | 378/62 |
| 5,437,280 A | 8/1995 | Hussman | 600/417 |
| 5,459,769 A | * 10/1995 | Brown | 378/4 |
| 5,595,177 A | 1/1997 | Mena et al. | 600/429 |
| 5,596,200 A | * 1/1997 | Sharma et al. | 250/370.14 |
| 6,647,283 B2 | * 11/2003 | Klotz | 600/425 |

FOREIGN PATENT DOCUMENTS

| | | |
|---|---|---|
| EP | 0799600 | 10/1997 |
| EP | 0972490 | 1/2000 |
| FR | 2786293 | 5/2000 |
| FR | 2786589 | 6/2000 |
| WO | 9744809 | 11/1997 |

OTHER PUBLICATIONS

Herbst et al, "Digital Tumor Fluoroscopy—A New Direct Imagining System in the Therapy Planning for Brain Tumors" International Journal J. Radiation Oncology Biol. Phys., Vol 18, pp. 221–231, No. 1 Jan.1990.

Chang et al, "Computed Tomographic Evaluation of the Breast", AM. J. of Roentgenology, V. 131, No. 5, Sep. 1978, pp 459–464.

* cited by examiner

*Primary Examiner*—David V. Bruce
*Assistant Examiner*—Therese Barber
(74) *Attorney, Agent, or Firm*—Jay L. Chaskin; Cantor Colburn LLP

(57) ABSTRACT

Method and apparatus for examination of a breast, in which a contrast medium is injected in the breast to be examined, an X-ray beam is emitted in the direction of the breast; a plurality of digital images of the X-ray beam is taken after it has crossed the breast, and a representative image of the contrast produced in the tissues of the breast is calculated from the digital images.

87 Claims, 7 Drawing Sheets

METHOD AND APPARATUS FOR RADIOLOGICAL EXAMINATION BY INJECTION OF A CONTRAST MEDIUM

CROSS REFERENCE TO RELATED APPLICATIONS

This application claims the benefit of a priority under 35 USC 119 to French Patent Application No. 0008870 filed Jul. 7, 2000, the entire contents of which are hereby incorporated by reference.

BACKGROUND OF THE INVENTION

The present invention concerns the field of imaging, notably medical, and in particular mammography.

A radiology apparatus used, for example, in mammography, RAD or RF conventional radiology and neurological or even vascular (peripheral or cardiac) radiology is generally composed of: an X-ray tube and a collimator for forming and delimiting an X-ray beam; an image receiver, generally a radiological image intensifier and a video camera, or even a solid-state detector; and a positioner carrying the X-ray tube and collimator assembly on one side and image receiver on the other, movable in space on one or more axes. An example of such an apparatus is shown in EP-A-972,490.

An X-ray tube mounted, for example, in a medical radiology apparatus comprises a cathode and an anode, both contained in a vacuum-tight envelope, for electric insulation between those two electrodes. The cathode produces an electron beam which is received by the anode on a small surface constituting a focus from which the X-rays are emitted. An example of such an apparatus is shown in WO-A-97/44809.

Ordinarily, for the purpose of tracking down possible breast cancer, X-ray images are analyzed in order to deduce therefrom an estimate of the probability of a lesion in given areas. Then, in case of detection of a suspicious area, a practitioner takes one or more biopsies in order to have tissues available for an histological analysis. A problem with the mammograms is the difficulty in detecting and analyzing lesions in radiologically dense breasts, especially when they are not accompanied by microcalcifications, for the mammographic images are projection images, each pixel of which represents the cumulative attenuation of the beam across the total thickness of the breast.

BRIEF DESCRIPTION OF THE INVENTION

An embodiment of the present invention seeks to reduce the number of biopsies which prove necessary and to increase the reliability of detection of lesions, by a high-quality visualization of breast lesions.

The method of examination of a breast, according to one aspect of the invention, comprises the steps of injection of a contrast medium in a breast to be examined, emission of an X-ray beam in the direction of the breast, taking a plurality of digital images of the X-ray beam after it has crossed the breast, and calculation of a representative image of the contrast produced in the tissues of the breast from the digital images.

The contrast medium can be injected in the blood vessels of a breast to be examined. The injection can be arterial or venous. Diffusion of the contrast medium is slower in the case of venous injection. The contrast medium can be iodine-based.

In an embodiment of the invention a first image is preferably taken before injection of the contrast medium.

In an embodiment of the invention at least one second image is taken after injection of the contrast medium.

In an embodiment of the invention, at least one second image is taken during a phase of heightened attenuation due to the contrast medium. Attenuation is understood to mean the diminution in number of X-photons when they cross the breast.

In an embodiment of the invention, at least one second image is taken after a phase of heightened attenuation due to the contrast medium.

In an embodiment of the invention, the second images are equally distributed in time. The second images are also called second image series.

In an embodiment of the invention, the second images are taken at shorter intervals during the phase of heightened attenuation due to the contrast medium than after the phase.

In an embodiment of the invention the number of second images can range between two and ten. In the second images, the gray level depends on the density of contrast medium in the breast.

In an embodiment of the invention a second image is preferably taken at the end of the heightened attenuation phase and a third image is taken a few minutes after the end of the phase.

In an embodiment of the invention the first image is advantageously subtracted from each of the second images. The subtracted images can be filtered spatially.

An embodiment of the invention is a radiology apparatus comprising means for injection of a contrast medium into a breast to be examined, means for emitting an energy beam, means for receiving the energy beam and sending an output a digital image representative of the incident energy beam, and means for processing for controlling the means for emitting and processing data from the means for receiving in order to calculate a representative image of the contrast produced in the cells of the breast from the digital images.

The means for processing is preferably capable of controlling the injection of a contrast medium after a first image is taken and before other images are taken. The means for processing can be capable of generating a representative image of the thickness of the contrast medium. The images can be converted into thickness images. A thickness image is understood to mean an image in which the gray level of the pixels depends on the thickness of the contrast medium.

An embodiment of the invention also directed to a computer program comprising means for providing program code for applying the steps of the method, when the program is working on a computer.

An embodiment of the invention is also directed to a storage medium capable of being read by a device reading the means for providing program code which are stored there and are suitable for use of the steps of the method, when the program is working on a computer.

BRIEF DESCRIPTION OF THE DRAWINGS

An embodiment of the invention is illustrated by the following drawings.

DETAILED DESCRIPTION OF THE INVENTION

The invention is applicable, in particular, to mammography, the object to be studied than being a breast that is examined with a view to determining whether certain areas are likely to be affected by a lesion which is, for example, cancerous. The areas affected show a vascularization different from that of healthy areas, glandular and adipose. Consequently, the kinetics of diffusion of a contrast medium injected in a blood vessel is different in a healthy area and an affected area. Study of that kinetics makes possible a rapid and reliable marking of the areas affected and helps determine the nature of the lesion, notably cancerous or not.

It is of particular interest to compare the frequency domain of maximum absorption of the contrast medium and the passband of a filter placed on output of the X-ray emitter. The filter makes it possible to approach the ideal case of monochromatic X-radiation.

A digital mammogram is taken with injection of a contrast medium and analysis of the diffusion of the contrast medium. Furthermore, even higher image quality can be obtained with a step of subtraction of an image taken before injection.

Figure 1:
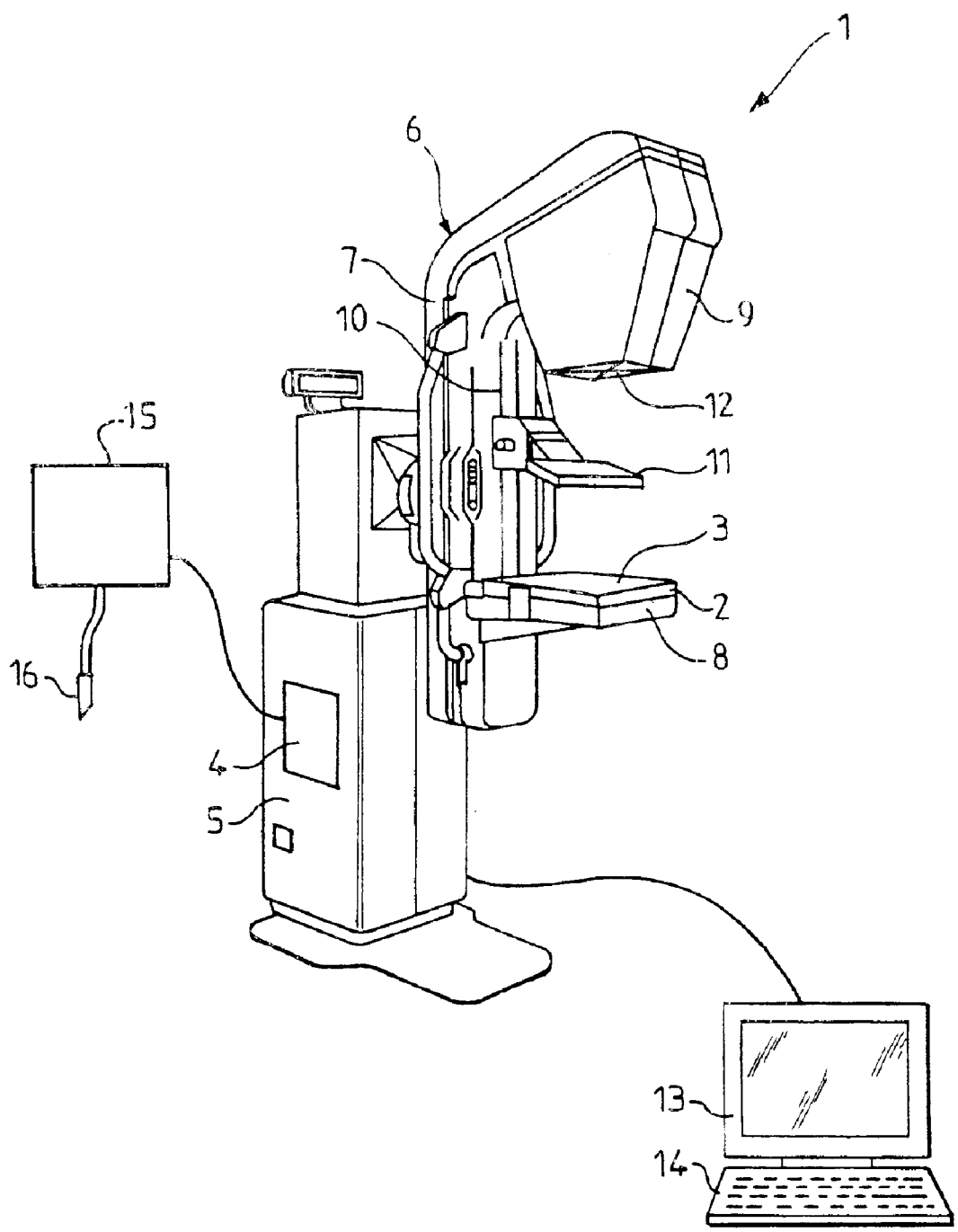
FIG. 1 is a schematic view of a radiographic device.

As illustrated in FIG. 1, a radiology device 1 includes a digital receiver 2, in the form, for example, of a solid state detector 3, suitable for taking digital images, and a processing and control unit 4. The radiology device 1 includes a base 5 standing on the floor and supporting a mobile assembly 6 rotating on the vertical plane of symmetry of the radiology device 1.

The assembly 6 includes a column 7 supporting a breast plate 8 of adjustable height connected to the receiver 2 and an X-ray emitting source 9. The column 7 is equipped on its front face with a fastening rail 10 of a compression pad 11 or holding plate. The X-ray source 9 is provided with a filter 12. The X-ray source 9 includes an anode and a cathode vacuum-sealed in a tight envelope and supplied with high voltage.

The processing and control unit 4 includes at least one microprocessor, at least one memory, at least one processing and/or control program stored in memory and capable of being executed by the microprocessor and a communication bus. The processing and control unit 4 is connected, notably, to the digital receiver 2, to the X-ray source 9 and to the filter 12.

The processing and control unit 4 can also include a screen 13 for display of images of the organ X-rayed and a keyboard 14.

In operation, the X-rays are emitted by the source 9, cross the filter 12, compression pad 11 and an organ and enter the digital receiver 2. The digital receiver 2 emits on output a representative image of the X-photons received and depending, therefore, on the characteristics of the beam emitted by the source 9, of the filter 12, of the organ, e.g., breast, to be examined and of the digital receiver 2 itself.

The processing and control unit 4 is connected to and capable of controlling a system of injection 15 of the contrast medium, such as a solution containing iodine and gadolinium, provided with a needle 16.

Figure 2:
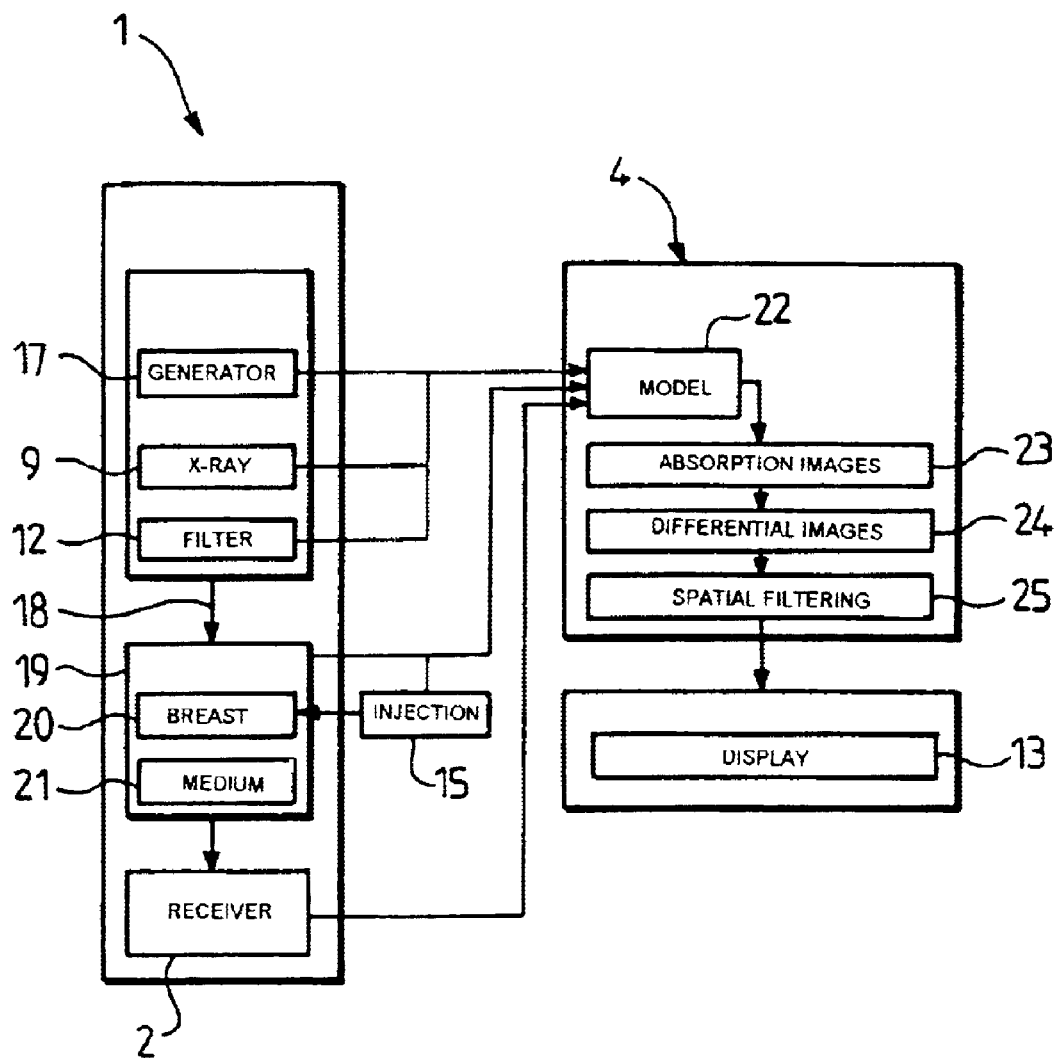
FIG. 2 is a functional diagram of the radiographic device.

In FIG. 2, the radiology device 1 is equipped with a high-voltage generator 17 for supply of the X-ray source 9. The X-ray beam 18 emitted below the filter 12 undergoes attenuation due to the object 19, an attenuation due to both the breast 20 and the contrast medium 21, with iodine base, for example, injected into the breast 20. The X-ray beam then reaches the digital receiver 2, an output of which is connected to the processing and control unit 4.

A model 22 provided in the processing and control unit 4 receives data from the digital receiver 2, generator 17, X-ray source 9 and filter 12 and data on the object under examination, such as the thickness of the breast and the time when the contrast medium was injected. The model 22 makes it possible to generate with these variables and images received from the digital receiver 2 an absorption image 23 expressed in physical units, such as the equivalent thickness of contrast medium, and no longer in gray level expressing arbitrary units like the raw image on output from the digital receiver 2.

The images 23 undergo a subtraction processing in order to obtain differential images 24. The differential images 24 undergo a spatial filtering like, for example, a local average making it possible to reduce the quantity of data to be processed and to reduce the noise. For each area having undergone an average, the progress of the image level is calculated, in other words, the progress of absorption of the contrast medium by the breast area corresponding to the image area in the course of time. A tracing of the progress can then be displayed on the screen 13.

Figure 3:
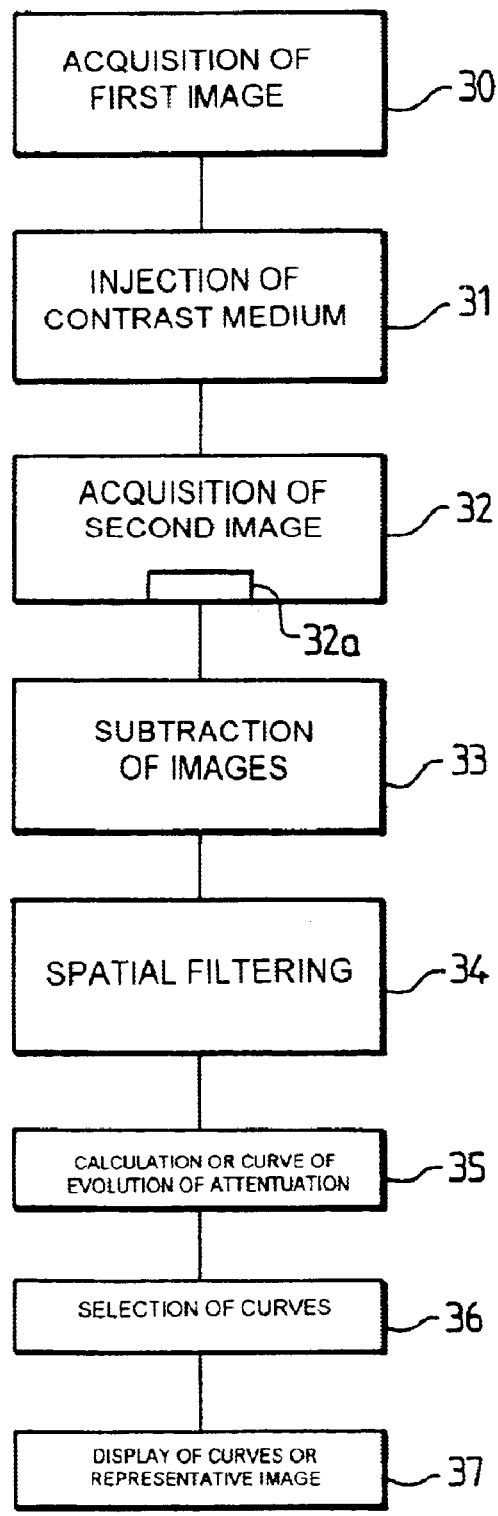
FIG. 3 is a flow chart of steps of the method.

The steps of the method illustrated in FIG. 3 is as follows:

In step 30, a first image is taken before injection of the contrast medium. A standard mammography image is then obtained, in which the lesions of the glandular tissue are difficult to distinguish from the healthy parts of the glandular tissue of the breast and the adipose tissue of the same breast.

In the subsequent step 31, the injection of contrast medium is done manually or by an injection system 15 illustrated in FIG. 1, controlled by the processing and control unit 4.

In the subsequent step 32, the processing and control unit 4 controls the acquisition of several images taken at regular time intervals or, on the other hand, at growing time intervals. In general, provision will be made for taking from two to ten images in the course of the step 32.

In step 33, a subtraction operation is carried out, in the course of which the first image taken in step 30 is removed from each image taken in step 32. The images taken in step 32 present a high contrast due to the diffusion and, therefore, the presence of the contrast medium in the breast. The contrast image can be converted into an image 32a in units of equivalent thickness of contrast medium. Examples of such a procedure are described in FR-A-2,786,293 or FR-A-2,786,589. The rate of subsequent digital processing is thus increased and the noise is reduced. The subtraction of images makes it possible to remove images taken in step 32, structures little vascularized and, therefore, little charged with contrast medium, the gray level of which little grows from the first image to the images taken in step 32. It is thus possible to maintain a high contrast, while reducing the noise. In other words, a differential image is calculated, a pixel of which has for its level $I\Delta = I(t1) - I(t0)$, with $I(t1)$ the level of the corresponding pixel of an image taken in step 32 and $I(t0)$ the level of the corresponding image taken in step 30.

In step 34, a spatial filtering is carried out, in other words, an average of several pixels in order to reduce the time of subsequent digital processing, knowing that a lesion is generally much larger than that of a pixel of the digital receiver 2.

In step 35, a curve of evolution of attenuation of the X-ray beam is calculated for each spatial area on which an average has been taken. The value of the maximum of the curve of that type can generally be considered a relatively reliable indicator of the probability of a lesion in the corresponding area.

In step 36, a selection of curves is made in order to mark the areas with strong probability of lesions.

In step 37, a display is made either of one of those curves or of a representative image of the maximum of the curves. It can also be based on the time elapsed between the instant of injection of the contrast medium and the instant at which the curve of attenuation as a function of time reaches its maximum.

By way of example, in case of an intravenous injection of contrast medium, if the time is in the order of one minute, the area considered has strong probabilities of containing a lesion. If the time is in the order of five minutes, it will be assumed that the corresponding area is normal and does not contain any lesion. This is due to the fact that lesions possess a denser vascularization than healthy glandular tissues. The contrast medium therefore spreads more rapidly and at higher concentration per surface or volume, depending on the type of imaging.

In order to obtain high image quality, it is advisable to choose the material constituting the anode of the X-ray source, the composition of the filter, the high voltage of supply and the contrast medium in a coordinated manner.

Figure 4:
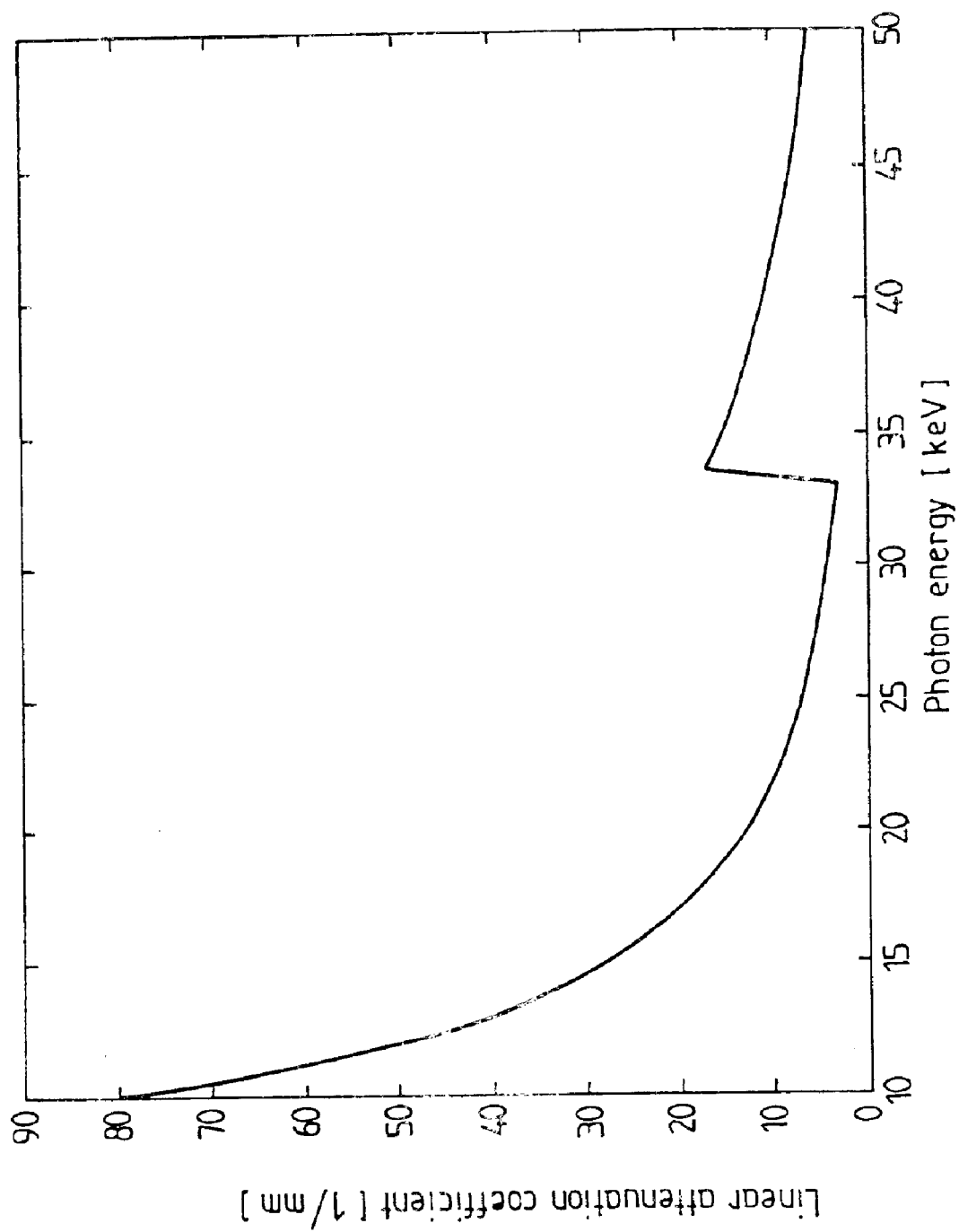
FIG. 4 is a linear attenuation curve of the contrast medium as a function of the X-ray energy.

For example, FIG. 4 shows the course of the linear attenuation coefficient of iodine, which can be used as contrast medium as a function of the X-ray energy expressed in keV. It can be observed that this attenuation curve presents a local maximum at around 33 keV, with a slow decline for higher values and a strong decline for lower values.

Figure 5:
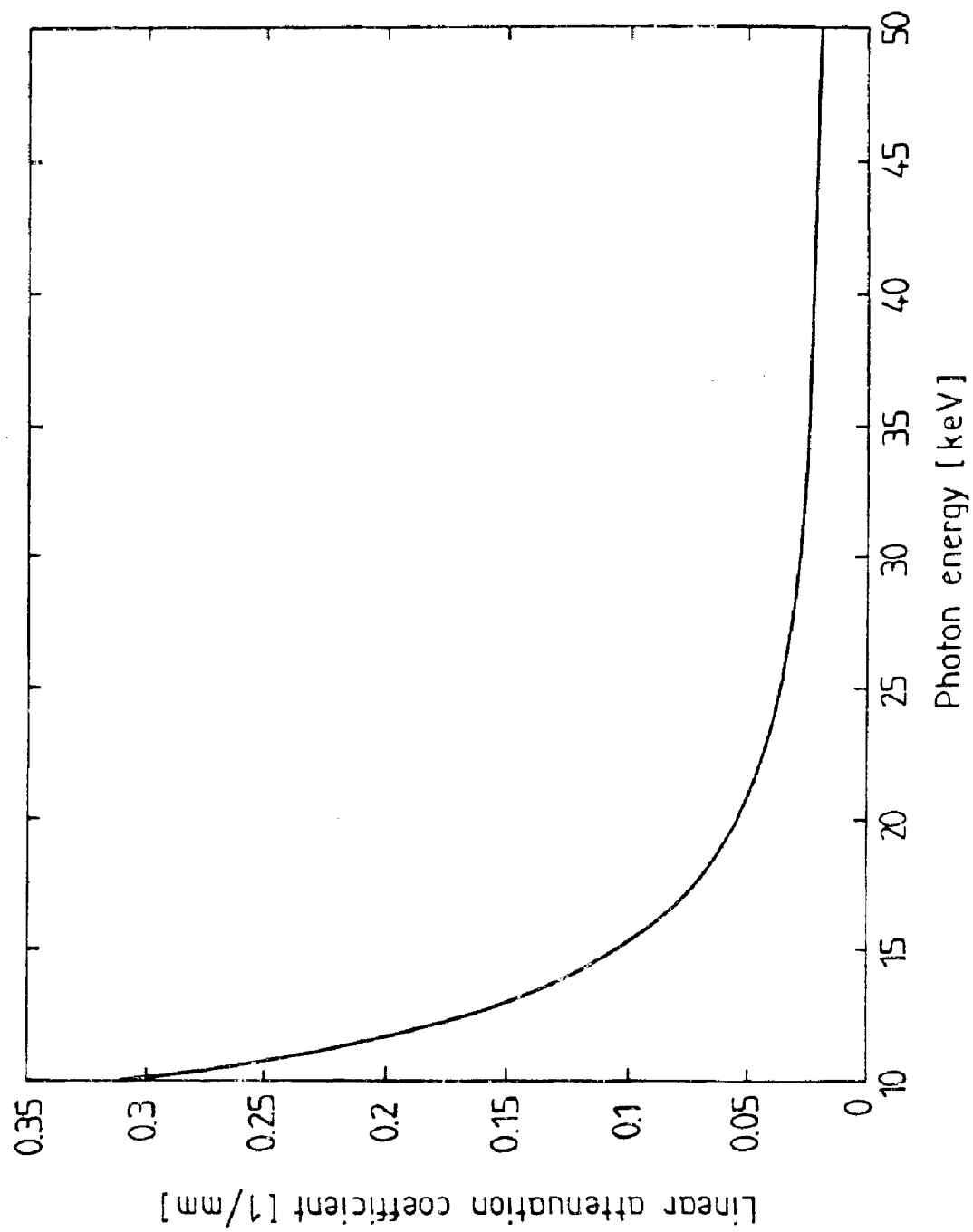
FIG. 5 is a linear attenuation curve of the adipose tissue as a function of the X-ray energy.

FIG. 5 illustrates the curve of the linear attenuation coefficient of an adipose tissue as a function of X-ray energy. The abscissa of the curves of FIGS. 4 and 5 is on the same scale. It can be seen that the adipose tissues present an extremely low attenuation coefficient for values in the order of 30 to 45 keV. That linear attenuation coefficient becomes greater for weak energies in the order of 10 keV or less.

In other words, in an area in the order of 33 to 45 keV, one will benefit from a weak attenuation due to the adipose tissue and which forms the noise of the image and a relatively strong attenuation due to the contrast medium which makes it possible to mark the areas of interest to the practitioner. The ratio of attenuation of iodine to attenuation of the adipose tissue is generally higher than 200 in the range of 33 to 45 keV.

Figure 6:
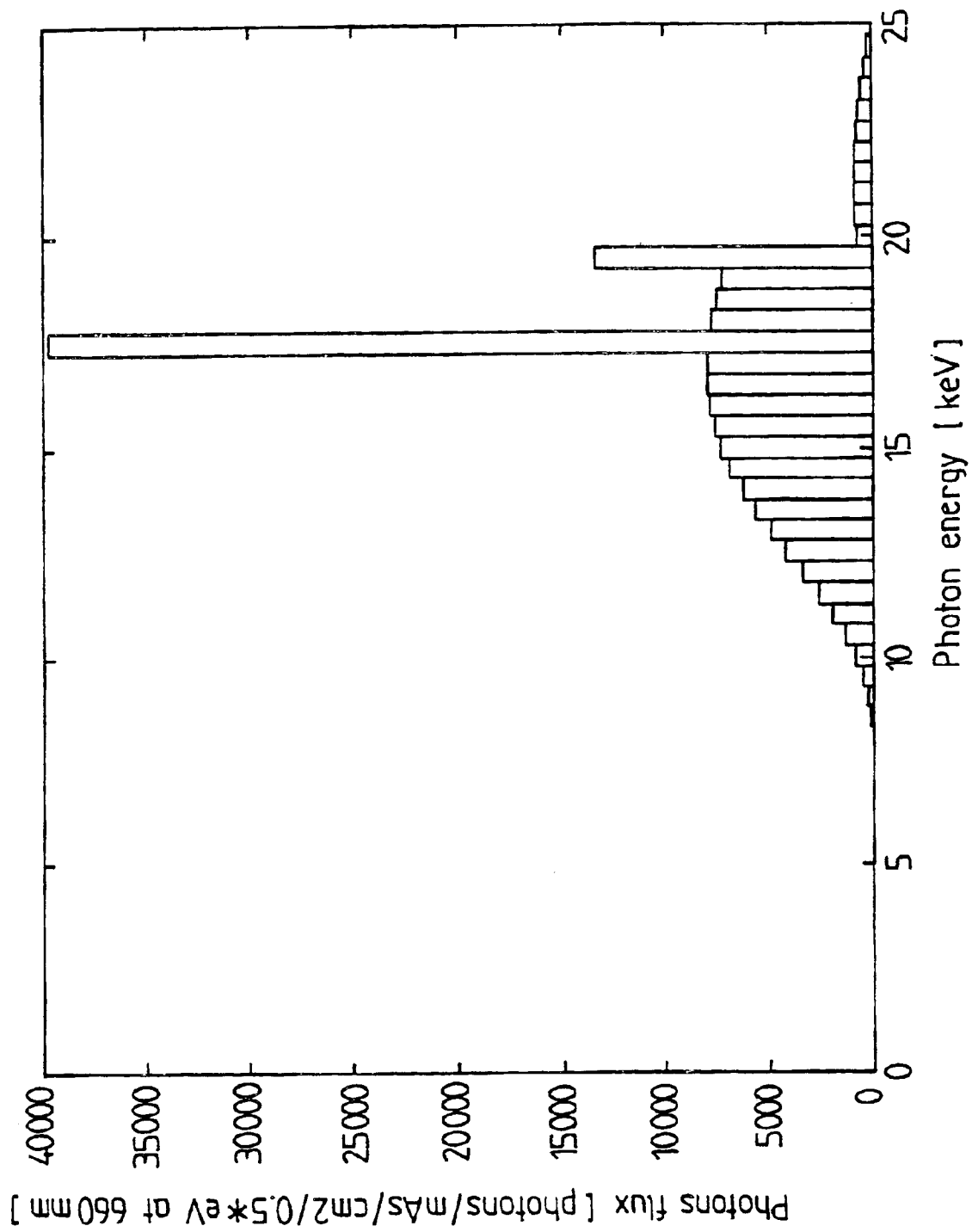
FIG. 6 is a curve showing a first example of the spectrum of an X-ray beam.

FIG. 6 illustrates the spectrum of an X-photon beam emitted by a mammography apparatus equipped with a molybdenum anode and molybdenum filter and supplied with voltage of 25 kV. The photon flux is particularly dense for energy values in the order of 15 to 20 keV.

Figure 7:
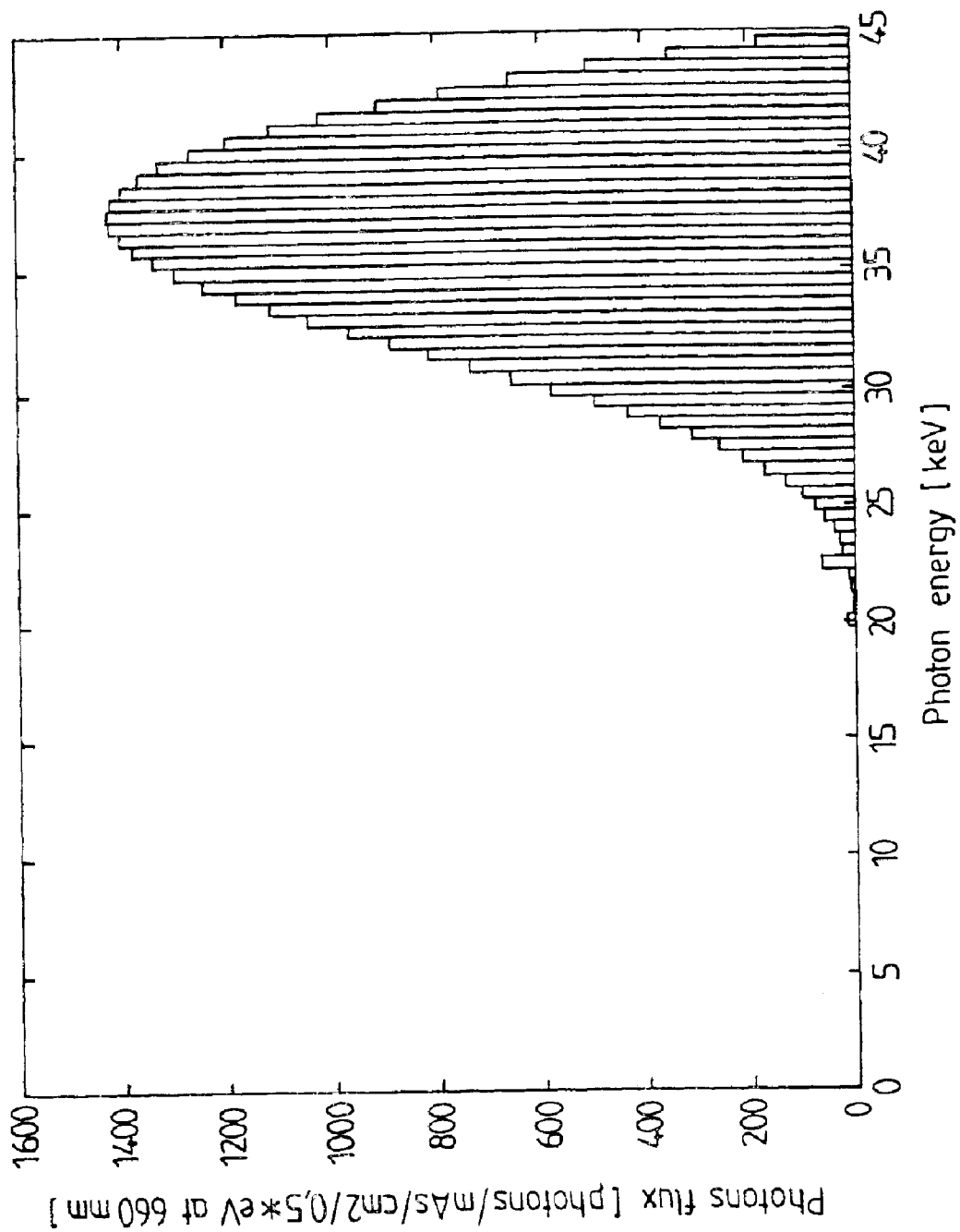
FIG. 7 is a curve showing a second example of the spectrum of an X-ray beam.

FIG. 7 illustrates the spectrum of an X-photon beam emitted by another mammography apparatus equipped with a rhodium anode and a copper filter 0.35 mm thick, supplied with a voltage of 45 kV. The photon flux is particularly dense for energy values ranging between 30 and 45 keV.

A photon flux of the type illustrated in FIG. 7 will therefore be used, which tallies well with the linear attenuation of iodine. In fact, iodine presents a K-absorption line around 33–35 keV, energy for which the photon flux is particularly dense in the case of FIG. 7.

More generally, a copper filter 0.2 to 0.5 mm thick and preferably 0.3 to 0.4 mm thick may be provided. The supply voltage may range between 40 and 50 kV and preferably between 45 and 49 kV. A filter containing zinc may also be envisaged.

One may likewise use a radiology apparatus with a rhodium anode and a filter containing a rhodium layer 25 microns thick and a copper layer 0.2 mm thick, or a tungsten anode with an aluminum filter 5 mm thick.

Thus, the different characteristics are matched, in the sense that it is sought to emit an X-ray beam with maximum intensity for a frequency in the same order as that of the K-absorption line of the contrast medium, a frequency at which the attenuation due to just the tissues of the breast will be particularly weak. It is thus possible to obtain high image quality, in regard to the elevated ratio between the absorption coefficient of the contrast medium in the frequency band used and the linear attenuation coefficient of the tissues of the breast. Furthermore, the noise of the images, which consists in part here of the attenuation due to the tissues of the breast, can be reduced as a result of subtraction of the first image.

It can also be arranged to calibrate the image so that the gray level of the image the practitioner displays on the screen is proportional to a quantity of iodine per unit of surface of the image. Interpretation of the images is thus greatly facilitated.

Finally, it is possible to obtain relatively low doses of radiation absorbed in the breast, in the order of 20% of those of a standard mammogram.

A relatively thick filter can be used in combination with a high supply voltage in order to obtain a spectrum which is close to the optimal spectrum of a monochromatic X-ray source of energy just above the K-absorption line of the contrast medium.

Various modifications in structure and/or steps and/or function may be made by one skilled in the art without departing from the scope of the invention.

What is claimed is:

1. A method for radiological examination of an organ comprising the steps of:
   (a) injecting a contrast medium into the organ to be examined;
   (b) emitting an energy beam in the direction of the organ;
   (c) taking a plurality of images after the energy beam has crossed the organ; wherein a first image is taken before injection of the contrast medium and at least one second image is taken after injection of the contrast medium during a phase of heightened attenuation due to the contrast medium; and
   (d) calculating a representative image of the contrast produced in the tissues of the organ from the images.

2. The method according to claim 1 in which the at least one second images are taken at intervals equally distributed in time.

3. The method according to claim 2 which the at least one second images are taken at shorter intervals of time during the phase of heightened attenuation due to the contrast medium than after the phase of heightened attenuation.

4. The method according claim 2 in which a second image is taken at the end of the attenuation phase and a third image is taken a few minutes after the end of the attenuation phase.

5. The method according to claim 2 which the first image is subtracted from each of the at least one second images.

6. The method according claim 3 in which at least one second image is taken at the end of the attenuation phase and a third image is taken a few minutes after the end of the attenuation phase.

7. The method according to claim 3 in which the first image is subtracted from each of the at least one second images.

8. The method according to claim 5 in which the subtracted images are filtered spatially.

9. The method according to claim 7 in which the subtracted images are filtered spatially.

10. The method according to claim 4 which the first image is subtracted from each of the at least one second images.

11. The method according to claim 6 in which the first image is subtracted from each of the at least one second images.

12. The method according to claim 1 in which the at least one second images are taken at shorter intervals of time during the phase of heightened attenuation due to the contrast medium than after the phase of heightened attenuation.

13. The method according claim 12 in which at least one second image is taken at the end of the attenuation phase and a third image is taken a few minutes after the end of the attenuation phase.

14. The method according to claim 13 in which the first image is subtracted from each of the second images.

15. The method according to claim 12 in which the first image is subtracted from each of the at least one second images.

16. The method according to claim 15 in which the subtracted images are filtered spatially.

17. The method according claim 1 in which at least one second image is taken at the end of the attenuation phase and a third image is taken a few minutes after the end of the attenuation phase.

18. The method according to claim 17 in which the first image is subtracted from each of the at least one second images.

19. The method according to claim 1 in which the first image is subtracted from each of the at least one second images.

20. The method according to claim 19 in which the subtracted images are filtered spatially.

21. The method according to claim 1 in which the images are converted into thickness images.

22. The method according to claim 1 wherein the examination is mammography.

23. The method of claim 1 wherein the emitting X-ray beam has a maximum intensity for a frequency in the same order as a selected absorption line of the contrast medium.

24. The method of claim 1 wherein a gray level of the at least one second image is proportional to a quantity of the contrast medium per unit surface of the image.

25. The method according to claim 1 wherein the number of at least one second images can range between 2 and 10.

26. The method according to claim 1 wherein a gray level of the at least one second image depends on the density of contrast medium in the organ.

27. The method according to claim 1 wherein the images are representative of the thickness of the contrast medium.

28. The method according to claim 21 wherein the images are representative of the thickness of the contrast medium.

29. A radiology apparatus comprising:
   means for injection of a contrast medium into an organ to be examined;
   means for emitting an energy beam;
   means for receiving the energy beam and capable of sending an output of a first image taken before injection of the contrast medium representative of the incident energy beam and at least one second image taken after injection of the contrast medium during a phase of heightened attenuation due to the contrast medium representative of the incident energy beam; and
   means for processing capable of controlling the means for emitting and processing data from the means for receiving in order to calculate a representative image of the contrast produced in the tissues of the organ from the images.

30. The apparatus according to claim 29 wherein the means for processing is capable of controlling the means for injection of a contrast medium after the acquisition of the first image and before the acquisition of other images.

31. The apparatus according to claim 30 wherein the means for processing is capable of generating a representative image of the thickness of the contrast medium.

32. The apparatus according to claim 30 in which the first image is subtracted from each of the at least one second images.

33. The apparatus according to claim 30 in which the at least one second images are taken at shorter intervals of time.

34. The apparatus according to claim 30 in which a second image is taken at the end of the attenuation phase and a third image is taken a few minutes after the end of the attenuation phase.

35. The apparatus according to claim 32 in which the subtracted images are filtered spatially.

36. The apparatus according to claim 29 wherein the means for processing is capable of generating a representative image of the thickness of the contrast medium.

37. The apparatus according to claim 29 in which the first image is subtracted from each of the at least one second images.

38. The apparatus according to claim 37 in which the subtracted images are filtered spatially.

39. The apparatus according to claim 29 in which the at least one second images are taken at intervals equally distributed in time.

40. The apparatus according to claim 29 in which the at least one second images are taken at shorter intervals of time.

41. The apparatus according to claim 29 in which a second image is taken at the end of the attenuation phase and a third image is taken a few minutes after the end of the attenuation phase.

42. The apparatus according to claim 29 wherein a gray level of the at least one second image is proportional to a quantity of the contrast medium per unit surface of the image.

43. The apparatus according to claim 29 wherein the number of second images can range between 2 and 10.

44. The apparatus according to claim 29 wherein a gray level of the at least one second image depends on the density of contrast medium in the organ.

45. The apparatus according to claim 29 in which the second images are taken at shorter intervals of time during the phase of heightened attenuation due to the contrast medium than after the phase of heightened attenuation.

46. The apparatus according to claim 29 wherein the emitting energy beam has a maximum intensity for a frequency in the same order as a selected absorption line of the contrast medium.

47. A method of radiological examination of an organ comprising the steps of:
(a) emitting an energy beam in the direction of the organ to be examined;
(b) taking a first image of the organ;
(c) injecting a contrast medium into the organ;
(d) taking at least one second image of the organ after the injection of the contrast medium, wherein the second image is taken during or after or at the end of a phase of heightened attenuation due to the contrast medium when the beam has crossed the organ;
(e) subtracting the first image from the second image; and
(f) calculating a curve of attenuation or a representative image of the contrast produced in the organ from the images.

48. The method according to claim 47 in which the at least one second images are taken at intervals equally distributed in time.

49. The method according to claim 47 in which the second images are taken at shorter intervals of time during the phase of heightened attenuation due to the contrast medium than after the phase of heightened attenuation.

50. The method according to claim 47 in which a second image is taken at the end of the attenuation phase and a third image is taken a few minutes after the end of the attenuation phase.

51. The method according to claim 47 in which the images are converted into thickness images.

52. The method according to claim 51 in which the subtracted images are filtered spatially.

53. The method according to claim 47 in which the first image is subtracted from each of the second images.

54. The method according to claim 47 in which the subtracted images are filtered spatially.

55. The method of claim 47 wherein a gray level of the at least one second image is proportional to a quantity of the contrast medium per unit surface of the image.

56. The method according to claim 47 wherein the number of second images can range between 2 and 10.

57. The method according to claim 47 wherein a gray level of the at least one second image depends on the density of contrast medium in the organ.

58. The method according to claim 47 wherein the images are representative of the thickness of the contrast medium.

59. The method according to claim 53 wherein the images are representative of the thickness of the contrast medium.

60. An article of manufacture comprising:
a computer useable medium having computer program code means embodied therein for taking radiological images by an apparatus having means for injection of a contrast medium into an object to be examined, means for emitting an energy beam, mean for receiving the energy beam and capable of sending an output of the images of the incident energy beam after the beam has crossed the object and means for processing capable of controlling the means for emitting and processing data from the means for receiving;
the computer readable program code means processing a first image taken before injection of the contrast medium;
the computer readable program code means processing at least one second image taken after the injection of the contrast medium during a phase of heightened attenuation due to the contrast medium; and
the computer readable program code means calculating a representative image produced in the object from the images.

61. The article according to claim 60 wherein the computer readable program code means processing the at least one second images at intervals equally distributed in time.

62. The article according to claim 60 wherein the computer readable program code means processing the at least one second image at shorter intervals of time during the phase of heightened attenuation due to the contrast medium than after the phase of the heightened attenuation.

63. The article according to claim 60 wherein the computer readable program code means processing the at least one second image at the end of the attenuation phase and third image a few minutes after the end of the attenuation phase.

64. The article according to claim 60 wherein the computer readable program code means processing in which the first image is subtracted from the at least one second image.

65. The article according to claim 60 wherein the computer readable program code means processing in which the first image is subtracted from each of the least one second images.

66. The article according to claim 64 wherein the computer readable program code means processing in which the subtracted images are filtered spatially.

67. The article according to claim 65 wherein the computer readable program code means processing in which the subtracted images are filtered spatially.

68. The article according to claim 60 wherein the computer readable program code means processing in which a gray level of the at least one second image is proportional to a quantity of the contrast medium per unit of surface of the image.

69. The article according to claim 60 wherein the computer readable program code means processing in which the number of second images can range between 2 and 10.

70. The article according to claim 60 wherein the article is a support capable of being read by a reading device for the computer readable program code means embodied therein.

71. The article of manufacture according to claim 60 wherein in the computer readable program code means the images is representative of the thickness of the contrast medium.

72. A program storage device readable by a machine, tangibly embodying a program of instructions executable by a machine to perform method steps for taking a radiological image of an object, the method steps comprising:
a. emitting an energy beam in the direction of the object to be examined;
b. taking a first image of the object;
c. injecting a contrast medium into the object;
d. taking at least one second image of the object after the injection of the contrast medium, wherein the second image is taken during or after or at the end of a phase of heightened attenuation due to the contrast medium when the beam has crossed the object;
e. subtracting the first image from the second image; and
f. calculating a curve of attenuation or a representative image of the contrast produced in the object from the images.

73. The program storage device according to claim 72 wherein the at least one second images are at intervals equally distributed in time.

74. The program storage device according to claim 72 wherein the at least one second image are at shorter intervals of time during the phase of heightened attenuation due to the contrast medium than after the phase of the heightened attenuation.

75. The program storage device according to claim 72 wherein the at least one second image is taken at the end of the attenuation phase and third image a few minutes after the end of the attenuation phase.

76. The program storage device according to claim 72 wherein the first image is subtracted from the at least one second image.

77. The program storage device according to claim 72 wherein the first image is subtracted from each of the at least one second image.

78. The program storage device according to claim 76 wherein the subtracted images are filtered spatially.

79. The program storage device according to claim 77 wherein the subtracted images are filtered spatially.

80. The program storage device according to claim 72 wherein a gray level of the at least one second image is proportional to a quantity of the contrast medium per unit of surface of the image.

81. The program storage device according to claim 72 wherein the number of second images can range between 2 and 10.

82. The program storage device according to claim 72 wherein the device is a support capable of being read by a program readable computer.

83. The program storage device according to claim 60 wherein the images are representative of the thickness of the contrast medium.

84. A computer program product for use with an image display device, the computer program product comprising:
   a. a computer useable medium having computer program code means embodied in the medium for causing a computer to take images of an object injected with a contrast medium, the computer program product having:
   b. computer readable program code means for causing the computer to take a first image before injection of the contrast medium;
   c. computer readable program code means for causing the computer to take at least one second image after the injection of the contrast medium during a phase of heightened attenuation due to the contrast medium; and
   d. computer readable program code means calculating a representative image produced in the object from the images.

85. The computer program product according to claim 84 wherein the computer readable program code means the images is representative of the thickness of the contrast medium.

86. A computer program product for use with a display device, the computer program product comprising:
   a. computer readable program code means for causing emission of an energy beam in the direction of an object to be examined;
   b. computer readable program code means for causing the taking of a first image of the object;
   c. computer readable program code means for causing injection of a contrast medium into the object;
   d. computer readable program code means for causing the taking of at least one second image of the object after the injection of the contrast medium, wherein the second image is taken during or after or at the end of a phase of heightened attenuation due to the contrast medium when the beam has crossed the object;
   e. computer readable program code means for causing the subtraction of the first image from the second image; and
   f. computer readable program code means for calculating a curve of attenuation or a representative image of the contrast produced in the object from the images.

87. The computer program product according to claim 86 wherein in the computer readable program code means the images is representative of the thickness of the contrast medium.

* * * * *